(12) United States Patent
Kulle

(10) Patent No.: US 8,761,902 B2
(45) Date of Patent: Jun. 24, 2014

(54) IMPLANTABLE ANCHOR FOR MEDICAL STIMULATION LEADS

(75) Inventor: Lee Kulle, Krugerville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 649 days.

(21) Appl. No.: 13/040,595

(22) Filed: Mar. 4, 2011

(65) Prior Publication Data

US 2011/0224764 A1    Sep. 15, 2011

Related U.S. Application Data

(60) Provisional application No. 61/312,811, filed on Mar. 11, 2010.

(51) Int. Cl.
*A61N 1/05* (2006.01)

(52) U.S. Cl.
USPC ........................................ 607/126; 607/150

(58) Field of Classification Search
USPC ......................................................... 607/126
See application file for complete search history.

(56) References Cited

U.S. PATENT DOCUMENTS

| | | | |
|---|---|---|---|
| 3,482,857 A | 12/1969 | Gohs | |
| 4,662,808 A * | 5/1987 | Camilleri | 411/340 |
| 5,273,053 A | 12/1993 | Pohndorf | |
| 6,473,654 B1 * | 10/2002 | Chinn | 607/126 |
| 6,554,802 B1 | 4/2003 | Pearson et al. | |
| 7,398,125 B2 | 7/2008 | Osypka et al. | |
| 7,591,970 B2 | 9/2009 | Olson | |
| 2005/0182464 A1 | 8/2005 | Schulte et al. | |
| 2007/0078399 A1 * | 4/2007 | Olson | 604/175 |

\* cited by examiner

*Primary Examiner* — Christopher D Koharski
*Assistant Examiner* — Natasha Patel

(57) ABSTRACT

In one embodiment, an anchor for anchoring a medical lead within the body of a patient, comprises: a first housing portion; a second housing portion, wherein the first and second housing portions define an inner passageway through the anchor and the inner passageway comprises first and second tapered portions at first and second ends of the inner passageway; and a gripping insert disposed within the inner passageway; wherein the first and second housing portions are adapted to be set in a first configuration and a second configuration by user manipulation; wherein in the first configuration, the inner passageway through the first and second housing portions permits the gripping insert to be retained in a first state; wherein in the second configuration, the gripping insert is compressed into a second state; wherein in the second configuration, the gripping insert is further compressed into a third state when the gripping insert is forced against one of the first and second tapered portions by movement of a medical lead placed in the anchor.

20 Claims, 3 Drawing Sheets

IMPLANTABLE ANCHOR FOR MEDICAL STIMULATION LEADS

CROSS-REFERENCE TO RELATED APPLICATIONS

This application claims the benefit of U.S. Provisional Application No. 61/312,811, filed Mar. 11, 2010, which is incorporated herein by reference.

TECHNICAL FIELD

The present application is generally related to an implantable anchor for anchoring an electrical stimulation lead, a drug infusion catheter, or other catheter of an implantable medical device system.

BACKGROUND

A number of implantable medical devices have been developed to deliver a variety of medical therapies through a medical lead. Typically, the distal end of the medical lead is implanted adjacent to a therapy site and a separately implanted medical device delivers the therapeutic agent to the therapy site via the medical lead.

In spinal cord stimulation (SCS) systems, a pulse generator is typically implanted within a subcutaneous pocket within the patient. An electrical lead is also implanted within the patient. The proximal end of the electrical lead is electrically coupled (either directly or via one or more extensions) to the pulse generator to receive electrical pulses from the pulse generator. The distal end of the electrical lead is positioned with electrodes of the lead disposed within the epidural space of the patient to deliver the electrical pulses to the spinal neural tissue of the patient. The efficacy of the electrical stimulation in treating chronic pain of the patient depends upon applying the electrical pulses to the appropriate neural tissue. Accordingly, it is desired to retain the stimulation lead at a relatively fixed position over time. An "anchor" structure is frequently sutured to tissue of the patient at a suitable site where the anchor further grips the stimulation lead to prevent migration or movement of the lead from the desired implant location.

Drug infusion implantable systems similarly employ catheters to allow various medical agents to be controllably infused after implantation of the respective system within a patient. For example, implantable medical systems are used or have been proposed for the infusion of insulin, opiates, anti-spasmodic drugs, intrahepatic chemotherapy agents, and other therapeutic agents in a number of countries subject to the regulatory requirements of those countries.

Implantable infusion systems typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes. To deliver the infusate from the reservoir, a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient). Anchor structures may also be employed to prevent migration of the infusion catheter so that infusate will continue to be delivered to the appropriate therapy site.

SUMMARY

DETAILED DESCRIPTION

Figure 1:
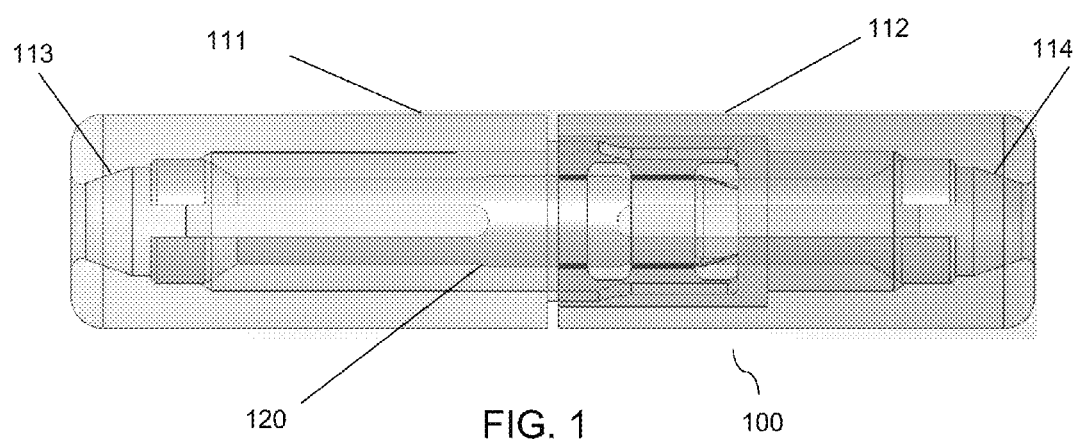
FIG. 1 depicts an anchor for anchoring a medical lead in a closed configuration according to one representative embodiment.

For the purposes of promoting an understanding of the principles of the present invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

Figure 2:
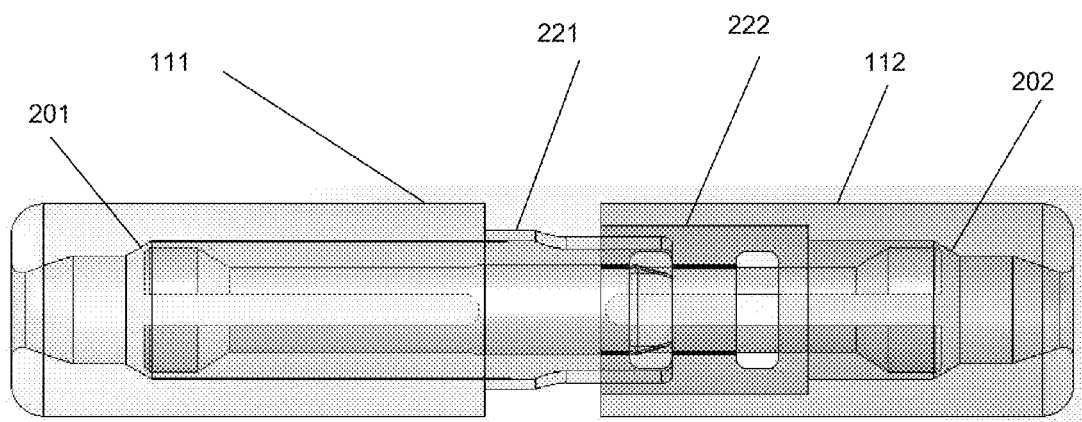
FIG. 2 depicts the anchor of FIG. 1 in an open configuration according to one representative embodiment.

FIGS. 1 and 2 depict anchor 100 for anchoring a medical lead according to one representative embodiment. Anchor 100 comprises housing portions 111 and 112 which define an inner passageway. Gripping insert 120 is disposed within the inner passageway. Anchor 100 may be placed in a closed configuration (as shown in FIG. 1) and may be placed in an open configuration (as shown in FIG. 2) by user manipulation. In the open configuration, anchor 100 may be slipped over the proximal end of a medical lead and advanced over the medical lead. In this configuration, gripping insert 120 is retained in a first, substantially non-compressed state and does not grip or otherwise hold onto the medical lead. When anchor 100 is placed in the closed configuration, gripping insert 120 is placed in a second state and compressed against the medical lead thereby gripping or holding the medical lead in place. That is, when placed in a closed configuration, anchor 100 grips the medical lead thereby generally preventing the medical lead from slipping longitudinally through anchor 100.

To accomplish the compression of gripping insert 120, anchor 100 comprises first housing portion 111 and second housing portion 112. Housing portions 111 and 112 are fitted together and are moveable relative to each other. In one preferred embodiment, housing portions 111 and 112 may be brought together by pushing, twisting, or otherwise translating housing portions 111 and 112 toward each other. As shown most clearly in FIG. 2, housing portions 111 and 112 respectively comprise inter-fitting portions 221 and 222 that are adapted to facilitate locking or snapping together of housing portions 111 and 112. In one preferred embodiment, inter-fitting portions 221 and 222 "snap" together and tend to stay in the closed configuration. For example, complementary structures on inter-fitting portions 221 and 222 may be adapted to snap or latch together. For example, one or more recesses may be formed in or on one of the housing portions and a raised feature on the other housing portion may be formed on the other housing portion to be placed within the recess when anchor 100 is placed in the closed position. Inter-fitting portions 221 and 222 may also be unlocked by application of sufficient pulling or twisting force in the opposition direction.

The interior of housing portions 111 and 112 are preferably adapted to control the compression of gripping insert 120 about the medical lead. In one embodiment, housing portions 111 and 112 respectively comprise a first set of tapered sections 201 and 202 (most clearly seen in FIG. 2) at the respective ends of anchor 100. When housing portions 111 and 112 are brought together (as shown in FIG. 1), the ends of gripping insert 120 contact tapered sections 201 and 202. The contact force between tapered sections 201 and 202 and the ends of gripping insert 120 causes a precise amount of compression of gripping insert 120 thereby controlling the gripping force applied to the medical lead.

Figure 7A:
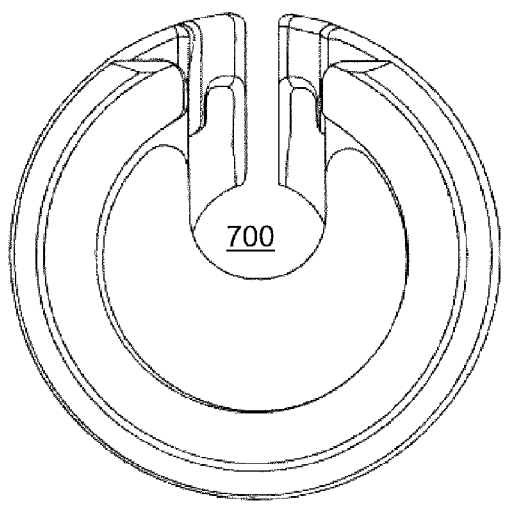
FIGS. 7A and 7B depict open and closed configurations for an inner lumen of the anchor of FIGS. 1 and 2 according to one representative embodiment.
Figure 7B:
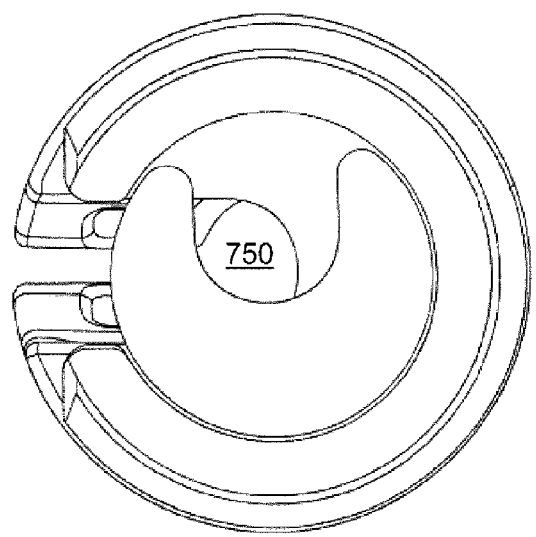

In an alternative embodiment, inter-fitting portions 221 and 222 of housing portions 111 and 112 may cause compression of gripping insert 120 about the medical lead in lieu or in addition to tapered sections 201 and 202. In one embodiment, inter-fitting portions 221 and 222 are adapted to comprise independently positioned inner lumens. When placed in the open configuration 700 as shown in FIG. 7A, the inner lumens may be co-aligned leaving gripping insert 120 uncompressed. In the closed configuration as shown in FIG. 7B, the respective inner lumens defined by inter-fitting portions 221 and 222 are placed in an eccentric or offset arrangement thereby restricting the passageway between the two portions 221 and 222. In the closed configuration, the reduced-size of the inner passageway compresses the medial portion of gripping insert 120 to grip the medical lead.

The interior of housing portions 111 and 112 preferably comprise a second set of tapered sections 113 and 114 (annotated in FIG. 1). The second set of tapered sections 113 and 114 reduces the inner diameter in a progressive manner from the smallest inner diameter defined by tapered sections 201 and 202. If a stretching force is applied to the medical lead after the medical lead is implanted and anchored by anchor 100, the stretching force will tend to pull on gripping insert 120. Gripping insert 120 would then contact one of tapered sections 113 and 114 thereby placing gripping insert 120 into a third state where it is further compressed about the medical lead. The adaptation to compress to an even small diameter in response to stretching forces is advantageous for selected types of medical leads as will be discussed below.

In certain embodiments, housing portions 111 and 112 of anchor 100 may be fabricated using a suitable polymer processing technique. The polymer or polymers are preferably adapted for long term implantation in a patient, i.e., biocompatibility and biostability. Also, the polymer preferably possesses a medium to high durometer to maintain the structural characteristics of anchor 100. An example of a suitable polymer for anchor 100 is polyetheretherketone (PEEK), although any biostable, biocompatible polymer having a suitable durometer and a suitable coefficient of friction can be employed.

In one embodiment, a combination of a relatively hard and soft (or flexible) material may be utilized. In this embodiment, an inner portion of housing portions 111 and 112 may be made from a relatively hard material, such as, but not limited to, PEEK or select metals. The outer portions of housing portions 111 and 112 may be fabricated from a more compliant material with a lower durometer value, such as silicone. Also, strain relief extensions (not shown) of a lower durometer material may extend from the ends of housing portions 111 and 112.

In one embodiment, housing portions 111 and 112 are not significantly deformed or compressed by suturing of anchor 100 to tissue of the patient. In this embodiment, when suturing is applied about the exterior of anchor 100, the suturing does not compress housing portions 111 and 112 in such a manner so as to transfer force to and compress gripping insert 120. Appropriate selection of the rigidity of the polymer material for housing portions 111 and 112 may accomplish this design feature. Further, in one embodiment, housing portions 111 and 112 may comprise suturing grooves or other features (not shown) to assist suturing of anchor 100 to patient tissue by the surgeon.

Figure 3:
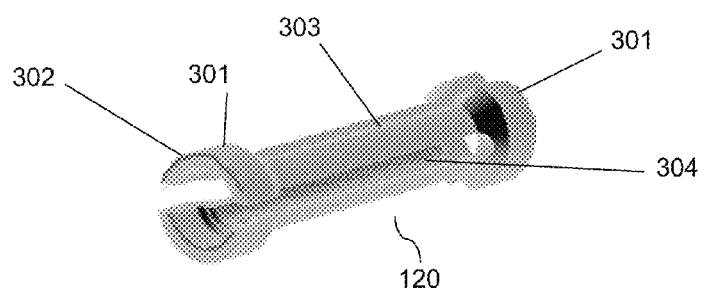
FIG. 3 depicts a gripping insert that may be employed within the anchor shown in FIGS. 1 and 2 according to one representative embodiment.

FIG. 3 depicts gripping insert 120 according to one representative embodiment. Gripping insert 120 comprises a plurality of beams 303 (only one is annotated for the sake of clarity) suspended between respective shoulders 301. An inner passageway is defined through the shoulders 301 and within the beams 303 for receiving the medical lead. Beams 303 are flexible relative to shoulders 301. Upon compression, beams 303 apply a gripping force onto the medical lead.

In one embodiment, gripping insert 120 is formed of titanium or a suitable titanium alloy, although any other suitable material may be employed. Gripping insert 120 may be fabricated using suitable processing techniques such as milling, machining, etc.

Figure 4:
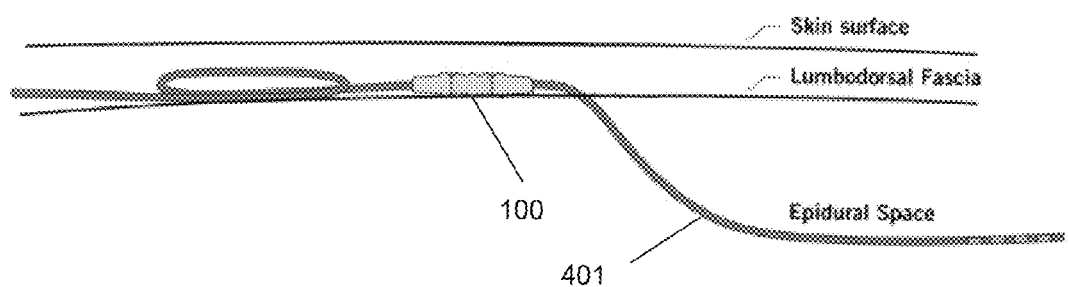
FIG. 4 depicts anchoring of a medical lead using the anchor of FIGS. 1 and 2 according to one representative embodiment.

FIG. 4 depicts example anchoring of a medical lead using the anchor of FIGS. 1 and 2 according to one representative embodiment. As shown in FIG. 4, medical lead 401 is implanted with its distal end disposed within the epidural space of the patient. Any suitable type of medical lead 401 may be employed including percutaneous-type leads and paddle-style leads. Medical lead 401 may be implanted using any suitable technique and, typically, percutaneous-type stimulation leads are provided within the epidural space through a suitable epidural needle. After the distal end of lead 401 is placed at the appropriate vertebral location and the needle is removed, anchor 100 is placed over the proximal end of the lead 401. Anchor 100 is adapted until anchor 100 is proximate to the entry point where the needle was previously inserted into the patient.

Anchor 100 is then placed within the closed or locked configuration about medical lead 401. Anchor 100 applies a gripping force against medical lead 401. Anchor 100 is sutured or otherwise attached to the lumbodorsal fascia of the patient. Thereby, various forces applied to medical lead 401 by various bodily movements of the patient will not tend to displace the distal end of medical lead 401 from the location in the epidural space for delivery of the medical therapy to the appropriate treatment location. Also, as shown in FIG. 4, a strain relief loop may be provided by the surgeon before the surgeon tunnels the proximal end of medical lead 401 underneath the skin for attachment to another suitable medical device (e.g., an "extension" or a pulse generator).

Figure 5:
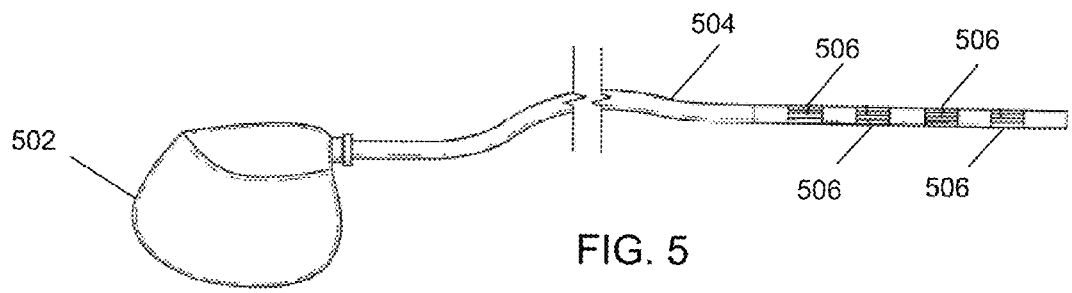
FIG. 5 depicts a conventional neurostimulation system that may utilize an anchor according to at least one representative embodiment.

Anchor 100 may be utilized in conjunction with any suitable implantable medical device that comprises a medical lead. For example, anchor 100 can be utilized to anchor an electrical stimulation lead of a neurostimulation system as shown in FIG. 5. Neurostimulation system 500 includes a pulse generator 502 and one or more stimulation leads 504.

Examples of a commercially available pulse generator are the EON® and EON MINI® products available from Advanced Neuromodulation Systems, Inc. An example of a commercially available stimulation lead is the AXXESS® lead available from Advanced Neuromodulation Systems, Inc.

The pulse generator 502 is typically implemented using a metallic housing that encloses circuitry for generating the electrical pulses for application to neural tissue of the patient. The pulse generator 502 is usually implanted within a subcutaneous pocket created under the skin by a physician. The lead 504 is used to conduct the electrical pulses from the implant site of the pulse generator for application to the targeted nerve tissue via electrodes 506. The lead 504 typically includes a lead body of an insulative polymer material with embedded wire conductors extending through the lead body. The electrodes 506 of the lead body are coupled to the conductors to deliver the electrical pulses to the nerve tissue. For example, the distal end of lead 504 may be positioned within the epidural space of the patient to deliver electrical stimulation to spinal nerves to treat chronic pain of the patient. Anchor 100 may be utilized to ensure that the distal end of the lead 504 remains adjacent to the appropriate nerves associated with the chronic pain or other condition of the patient. In some embodiments, an "extension" lead (not shown) may be utilized as an intermediate connector, if deemed appropriate by the physician.

In certain embodiments, lead 504 is a "body compliant" lead that possesses mechanical characteristics that allow the lead 504 to elastically stretch in response to forces experienced with the patient's body. Also, after removal of the stretching force, lead 504 is capable of resuming its original length and profile. For example, lead 504 may stretch 10%, 20%, 25%, 35%, or even up or above to 50% at forces of about 0.5, 1.0, and/or 2.0 pounds of stretching force. The ability to elongate may be obtained by suitably modifying the helically wrapping of the wire conductors within lead 504 and by selecting a suitable elastic, low durometer polymer material (e.g. CARBOSIL™ a silicone polycarbonate urethane) for the lead body. Fabrication techniques and material characteristics for "body compliant" leads are disclosed in greater detail in U.S. Provisional Patent Application Ser. No. 60/788, 518, entitled "Lead Body Manufacturing," filed Mar. 31, 2006, which is incorporated herein by reference for all purposes.

The ability to elongate at relatively low forces may present one or more advantages for implantation in a patient. For example, as a patient changes posture (e.g., "bends" the patient's back), the distance from the implanted pulse generator to the stimulation target location changes. Lead 504 may elongate in response to such changes in posture without damaging the components lead 504 or disconnecting from the pulse generator 502.

Anchor 100 is advantageous for such elastic leads. Specifically, when a stretching force is applied to lead 504, the outer diameter of lead 504 may be reduced. The reduction in the outer diameter may be especially pronounced at a pressure point within a conventional anchor. In such a situation, the reduction in outer diameter may cause lead 504 to slip out from anchor 100. In other cases, the dislocation of lead 504 from a conventional anchor may be quite small for a single, change in posture by the patient. However, over time, repeated changes in posture may cause the anchor 100 to move in a "ratchet" like manner. Eventually, electrodes 506 of lead 504 may be dislocated from their desired position adjacent to neural tissue of the patient. Unlike conventional anchors, anchor 100 is adapted to resist dislocation of the lead. Specifically, the size of its inner passageway of gripping insert 120 is reduced to prevent a reduction in the diameter of lead 504 from permitting lead 504 to slip through anchor 100.

Figure 6:
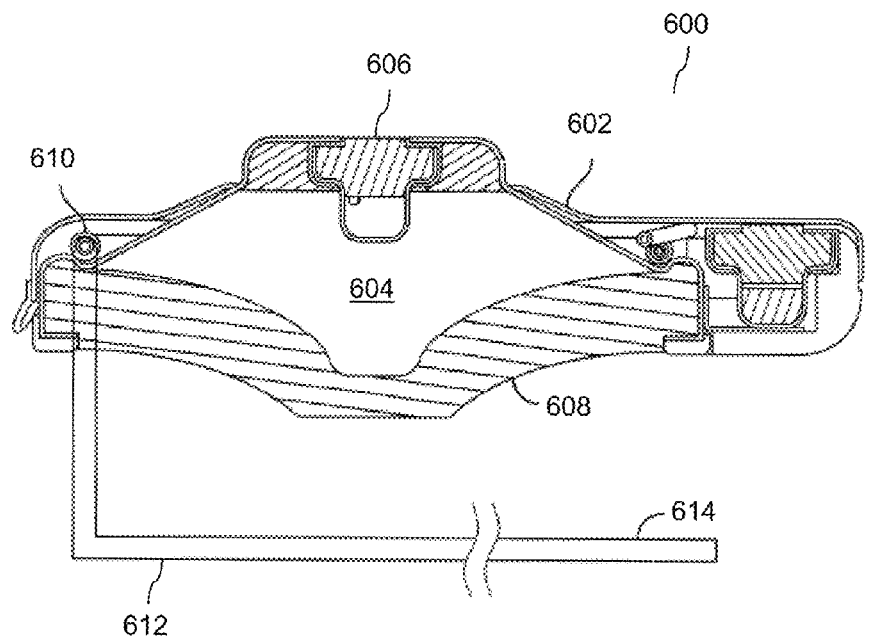
FIG. 6 depicts a conventional drug pump system that may utilize an anchor according to at least one representative embodiment.

Alternatively, anchor 100 can be utilized to anchor an infusion catheter of an implantable drug infusion device 600 as shown in FIG. 6. The implantable infusion drug pump device 600 may include a central housing 602, a reservoir 604 to hold the infusate, a septum 606 to allow infusate to be introduced into the reservoir, an energy source 608 (e.g., a spring diaphragm) to drive the infusate from the reservoir and through an outlet port 610, and various flow control elements (not shown).

The central housing 602 of the device is often implanted in a suitable subcutaneous region with the septum 606 positioned immediately below the skin of the patient to facilitate access to the reservoir 604 for refilling purposes. A catheter 612 is attached to the outlet port 610 of the central housing 602 to receive the infusate outflow. A distal end 614 of the catheter is implanted within the patient adjacent to the appropriate therapy site. Anchor 100 may be utilized to ensure that the distal end 614 of the lead 612 remains adjacent to the appropriate site associated with the chronic pain of the patient.

Although some representative embodiments have been discussed in terms of anchoring intrathecal and epidural catheters and leads, anchors can be employed according to alternative embodiments for any suitable location. For example, an anchor according to some embodiments could be used for peripheral nerve stimulation and gastric pacing applications. Also, it shall be appreciated that the use of the term "medical lead" is to be understood in a broad sense as encompassing any implantable electrical stimulation lead, catheter, medical sensing lead, or the like.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. An implantable anchor for anchoring a medical lead within the body of a patient, comprising:
    a first housing portion;
    a second housing portion, wherein the first and second housing portions define an inner passageway through the anchor and the inner passageway comprises first and second tapered portions at first and second ends of the inner passageway; and
    a gripping insert disposed within the inner passageway;
    wherein the first and second housing portions are adapted to be set in a first configuration and a second configuration by user manipulation;
    wherein in the first configuration, the inner passageway through the first and second housing portions permits the gripping insert to be retained in a first state;
    wherein in the second configuration, the gripping insert is compressed into a second state;

wherein in the second configuration, the gripping insert is further compressed into a third state when the gripping insert is forced against one of the first and second tapered portions by movement of a medical lead placed in the anchor;

wherein the first and second housing portions are adapted to permit a user to twist the first and second housing portions from the first configuration and to lock the first and second housing portions in the second configuration.

2. The implantable anchor of claim 1 wherein the inner passageway comprises third and fourth tapered portions adapted to compress the gripping insert into the second state.

3. The implantable anchor of claim 1 wherein an inner diameter of the inner passageway is reduced about the medial portion of the gripping insert in the second configuration.

4. The implantable anchor of claim 1 wherein the first and second housing portions are laterally translated relative to each other when placed in the second configuration.

5. The implantable anchor of claim 1 wherein the gripping insert comprises a plurality of compressible beams joined together by shoulders at each end of the gripping insert.

6. The implantable anchor of claim 5 wherein the shoulders comprise a beveled portion to contact the first and second tapered portions of the inner passageway.

7. The implantable anchor of claim 1 wherein the gripping insert is formed from a titanium material.

8. The implantable anchor of claim 1 wherein the first and second housing portions comprise suture grooves.

9. The implantable anchor of claim 8 wherein the first and second housing portions are formed from a sufficiently rigid material to prevent exterior forces from applied sutures from compressing the gripping insert.

10. A method of fabricating an implantable anchor for anchoring a medical lead within the body of a patient, the method comprising:
providing a first housing portion and a second housing portion, wherein (i) the first and second housing portions define an inner passageway through the anchor and the inner passageway comprises first and second tapered portions at first and second ends of the inner passageway, (ii) the first and second housing portions are adapted to be set in a first configuration and a second configuration by user manipulation, and (iii) wherein the first and second housing portions are adapted to permit a user to twist the first and second housing portions from the first configuration and to lock the first and second housing portions in the second configuration; and
providing a gripping insert disposed within the inner passageway, wherein (i) in the first configuration, the inner passageway through the first and second housing portions permits the gripping insert to be retained in a first state, (ii) wherein in the second configuration, the gripping insert is compressed into a second state to grip a medical lead disposed within the anchor, and (iii) wherein in the second configuration, the gripping insert is further compressed into a third state when the gripping insert is forced against one of the first and second tapered portions by movement of a medical lead placed in the anchor.

11. The method of claim 10 wherein the inner passageway comprises third and fourth tapered portions adapted to compress the gripping insert into the second state.

12. The method of claim 10 wherein an inner diameter of the inner passageway is reduced about the medial portion of the gripping insert in the second configuration.

13. The method of claim 10 wherein the first and second housing portions are laterally translated relative to each other when placed in the second configuration.

14. The method of claim 10 wherein the gripping insert comprises a plurality of compressible beams joined together by shoulders at each end of the gripping insert.

15. The method of claim 14 wherein the shoulders comprise a beveled portion to contact the first and second tapered portions of the inner passageway.

16. The method of claim 10 wherein the gripping insert is formed from a titanium material.

17. The method of claim 10 wherein the first and second housing portions comprise suture grooves.

18. The method of claim 17 wherein the first and second housing portions are formed from a sufficiently rigid material to prevent exterior forces from applied sutures from compressing the gripping insert.

19. An implantable anchor for anchoring a medical lead within the body of a patient, comprising:
a first housing portion;
a second housing portion, wherein the first and second housing portions define an inner passageway through the anchor and the inner passageway comprises first and second tapered portions at first and second ends of the inner passageway; and
a gripping insert disposed within the inner passageway;
wherein the first and second housing portions are adapted to be set in a first configuration and a second configuration by user manipulation;
wherein in the first configuration, the inner passageway through the first and second housing portions permits the gripping insert to be retained in a first state;
wherein in the second configuration, the gripping insert is compressed into a second state;
wherein in the second configuration, the gripping insert is further compressed into a third state when the gripping insert is forced against one of the first and second tapered portions by movement of a medical lead placed in the anchor;
wherein the first and second housing portions are laterally translated relative to each other when placed in the second configuration.

20. The implantable anchor of claim 19 wherein an inner diameter of the inner passageway is reduced about the medial portion of the gripping insert in the second configuration.

* * * * *